(12) United States Patent
Villard

(10) Patent No.: US 9,013,241 B2
(45) Date of Patent: Apr. 21, 2015

(54) CIRCUIT FOR MEASURING THE RESONANT FREQUENCY OF NANORESONATORS

(71) Applicant: Commissariat a l'Energie Atomique et aux Energies Alternatives, Paris (FR)

(72) Inventor: Patrick Villard, Grenoble (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 13/970,332

(22) Filed: Aug. 19, 2013

(65) Prior Publication Data

US 2014/0055203 A1    Feb. 27, 2014

(30) Foreign Application Priority Data

Aug. 22, 2012   (FR) ...................................... 12 57931

(51) Int. Cl.
| | |
|---|---|
| *H03B 5/30* | (2006.01) |
| *H03L 7/081* | (2006.01) |
| *G01G 3/16* | (2006.01) |
| *G01H 13/00* | (2006.01) |
| *H03L 7/07* | (2006.01) |
| *G01N 29/12* | (2006.01) |
| *G01N 29/36* | (2006.01) |
| *G01N 3/16* | (2006.01) |
| *G01N 29/036* | (2006.01) |

(52) U.S. Cl.
CPC *H03L 7/081* (2013.01); *G01N 3/16* (2013.01); *G01N 29/036* (2013.01); *G01G 3/16* (2013.01); *G01H 13/00* (2013.01); *H03B 5/30* (2013.01); *H03L 7/07* (2013.01); *H03L 7/0812* (2013.01); *G01N 29/12* (2013.01); *G01N 29/36* (2013.01); *G01N 2291/0256* (2013.01)

(58) Field of Classification Search
CPC    G01G 3/16; G01N 2291/0256; G01N 29/036
USPC ............... 73/32 A, 504.12, 504.15, 579, 580; 331/154, 116 M, 96
See application file for complete search history.

(56) References Cited

U.S. PATENT DOCUMENTS

| | | | |
|---|---|---|---|
| 6,041,642 A | 3/2000 | Duncan | |
| 6,722,200 B2 * | 4/2004 | Roukes et al. | ................. 73/580 |
| 2005/0052813 A1 | 3/2005 | Kobayashi | |

FOREIGN PATENT DOCUMENTS

WO    02090246 A2    11/2002

* cited by examiner

*Primary Examiner* — Arnold Kinkead
(74) *Attorney, Agent, or Firm* — Baker & Hostetler LLP

(57) ABSTRACT

The present disclosure relates to nanoresonator oscillators or NEMS (nanoelectromechanical system) oscillators. A circuit for measuring the oscillation frequency of a resonator is provided, comprising a first phase-locked feedback loop locking the frequency of a controlled oscillator at the resonant frequency of the resonator, this first loop comprising a first phase comparator. Furthermore, a second feedback loop is provided which searches for and stores the loop phase shift introduced by the resonator and its amplification circuit when they are locked at resonance by the first loop. The first and the second loops operate during a calibration phase. A third self-oscillation loop is set up during an operation phase. It directly links the output of the controllable phase shifter to the input of the resonator. The phase shifter receives the phase-shift control stored by the second loop.

14 Claims, 7 Drawing Sheets

CIRCUIT FOR MEASURING THE RESONANT FREQUENCY OF NANORESONATORS

CROSS-REFERENCE TO RELATED APPLICATION

This application claims priority to foreign French patent application No. FR 1257931, filed on Aug. 22, 2012, the disclosure of which is incorporated by reference in its entirety.

FIELD OF THE INVENTION

The invention relates to circuits with micro-machined electromechanical resonators and in particular to nanoresonator oscillators or NEMS (nanoelectromechanical systems) oscillators. These systems integrate, on one substrate, mechanical elements, micromachined to nanometer scale by collective microelectronics fabrication technologies.

These circuits can be used notably for measuring very small weights, typically between $10^{-24}$ and $10^{-21}$ grams. The applications targeted are, for example, gas analysis or mass spectrometry.

BACKGROUND

In such systems that use resonators, the signal to be measured is the resonant frequency of the nanoresonator, in fact depending directly on the weight of matter deposited on the resonator, a greater weight generating a lower resonant frequency.

To measure the resonant frequency, it has already been proposed to use a self-oscillating circuit comprising a closed oscillation loop incorporating the resonator. FIG. 1 schematically represents such a self-oscillating circuit. The self-oscillating loop comprises the resonator NMS in series with an amplification and phase-shifting subsystem, and a feedback between the output of the subsystem and an excitation input of the resonator. The amplification subsystem adds a gain by an amplifier AMP and a phase shift by a phase shifter DPH; it makes it possible to ensure natural oscillation conditions (open loop gain greater than or equal in modulus to 1 for a loop phase shift that is a multiple of $2\pi$). The oscillation frequency is the natural mechanical resonant frequency of the resonator NMS. It is measured at the end of the amplification subsystem by a frequency meter FMTR. The latter can operate, for example, on the principle of counting pulses of a reference clock CLK that has a frequency very much greater than the oscillation frequency. The analogue or digital output S of the frequency meter supplies a measurement of the natural resonant frequency of the resonator. This solution makes it possible to produce circuits with little bulk, which is important notably in the case where the aim is to produce a network comprising a large number of nanoresonators. However, since there is a wide technological dispersion in the resonators and the components of the amplification subsystem, it is difficult to guarantee a priori that gain and phase conditions will be obtained that allow for a spontaneous natural oscillation at the resonant frequency.

Phase-locked loop (PLL loop) circuits have also been proposed, such as the one schematically represented in FIG. 2. The circuit also comprises a nanoresonator NMS in series with an amplifier AMP, a voltage-controlled oscillator (VCO) or a digitally-controlled oscillator (DCO) for exciting the resonator (NMS), a phase comparator CMPH, and a subtractor SUB for subtracting from the output of the phase comparator a value (modulo $2\pi$) which represents the natural phase shift $\Delta\Phi\text{ref}$ introduced by the resonator and the amplifier at the resonant frequency. A low-pass filter FLTR is inserted between the output of the phase comparator and a control input of the oscillator to ensure the stability of the locked loop.

The value $\Delta\Phi\text{ref}$ is a phase-shift value measured by calibration by having the resonator and the amplifier operate in open loop mode at the resonant frequency and by observing the phase shift between the excitation signal of the resonator and the output of the amplifier.

The circuit is automatically locked on to the frequency for which the phase shift between the inputs of the phase comparator is equal to $\Delta\Phi\text{ref}$; this frequency is the natural resonant frequency of the resonator. In practice, in closed loop mode, the output of the phase comparator represents the phase shift of the resonator and of the amplifier. If it is not equal to $\Delta\Phi\text{ref}$, the control voltage of the oscillator VCO is adjusted until it becomes equal to $\Delta\Phi\text{ref}$, the phase shift corresponding to resonance. The measurement of the resonant frequency is then done by measuring the control voltage Vout of the oscillator, this voltage representing the oscillation frequency of the oscillator. This solution with PLL loop requires a preliminary calibration to know the phase shift $\Delta\Phi\text{ref}$ at resonance.

The circuits using such a phase-locked loop consume more current than the circuits that operate in natural oscillation mode. Also, they are bulky.

SUMMARY OF THE INVENTION

One aim of the invention is to produce a resonant frequency measurement circuit which benefits from the advantages of PLL circuits to guarantee an enforced oscillation at the resonant frequency, despite the technological dispersions, but which consumes less energy and which can be produced with less bulk in the case where a large number of networked resonators NEMS are used in parallel.

According to the invention, an electronic circuit for measuring the oscillation frequency of a resonator is proposed, comprising a first feedback loop which is a phase-locked loop comprising the resonator, a controlled-frequency oscillator and a first phase comparator, this loop locking the frequency of a controlled oscillator at the resonant frequency of the resonator, the measurement circuit also comprising:

- a second feedback loop comprising a controllable phase shifter, a second phase comparator receiving the output of the controlled oscillator and the output of the controllable phase shifter, the second phase comparator supplying a control signal for the phase shifter acting in a direction tending to reduce to zero the phase shift between its inputs, means being provided for storing the phase-shift control obtained,
- a third loop which is a self-oscillation loop, comprising the resonator and the controllable phase shifter and linking the output of the controllable phase shifter to the input of the resonator,
- and means for activating the first loop and the second loop and deactivating the third loop, during a calibration phase, and for deactivating the first and the second loops and activating the third loop, during an operation phase, the control of the controllable phase shifter during the operation phase being the control stored at the end of the calibration phase.

The first feedback loop preferably comprises the resonator in series with an amplifier, the first phase comparator receiving, on one input, the output of the amplifier and, on another input, the output of the controlled-frequency oscillator and supplying a measurement of the phase shift between its inputs, a subtractor for subtracting from this measurement of the phase shift a reference phase-shift value, the output of the subtractor controlling the controlled oscillator.

Overall the circuit according to the invention operates as follows:

in a calibration phase, the third loop is deactivated, that is to say the link is cut between the output of the controlled phase shifter and the excitation input of the resonator; the latter is controlled only by the output of the controlled oscillator, which is locked by the first feedback loop. The resonator enters into resonance by virtue of this first loop which is active. The second feedback loop, also active, determines the real phase difference which then exists (at resonance) between the excitation input of the resonator and the output of the amplifier. This phase difference is stored; it is a difference such that the sum of this difference and of the phase shift of the resonator and of the amplifier is a multiple of $2\pi$;

in an operation phase, the first and the second feedback loops are neutralized, but the phase difference measured in the calibration phase is kept in memory for use during the operation phase; a stored phase control is applied to the controllable phase shifter; the third loop is re-enabled by linking the output of this phase shifter to the input of the resonator; the third loop enters into oscillation at the resonant frequency because the loop phase shift is a multiple of $2\pi$.

A low-pass filter can be provided in the first loop between an output of the subtractor and a control input of the controlled oscillator, and another low-pass filter can be provided in the second feedback loop between an output of the second phase comparator and the control storage means of the phase shifter.

A fourth feedback loop, enabled during the calibration phase, can be provided to establish a gain control signal for the amplifier such that the gain of the subsystem comprising the resonator, the amplifier, and the phase shifter is greater than 1 during the calibration phase; a means is then provided for storing this gain control signal and for applying the stored control signal to the amplifier during the operation phase.

The invention is particularly applicable to measuring the frequency of multiple resonators organized in a network of rows and columns. The third loop is then individual for each resonator and is addressable by a row conductor common to the resonators of one and the same row. By contrast, the first and the second feedback loops are common to the resonators of one and the same column and are linked, by respective column conductors, common to the resonators of one and the same column, to the components of that of the third loops which is addressed by a row conductor.

BRIEF DESCRIPTION OF THE DRAWINGS

Other features and advantages of the invention will become apparent on reading the following detailed description which is given with reference to the appended drawings in which.

DETAILED DESCRIPTION

Figure 3:
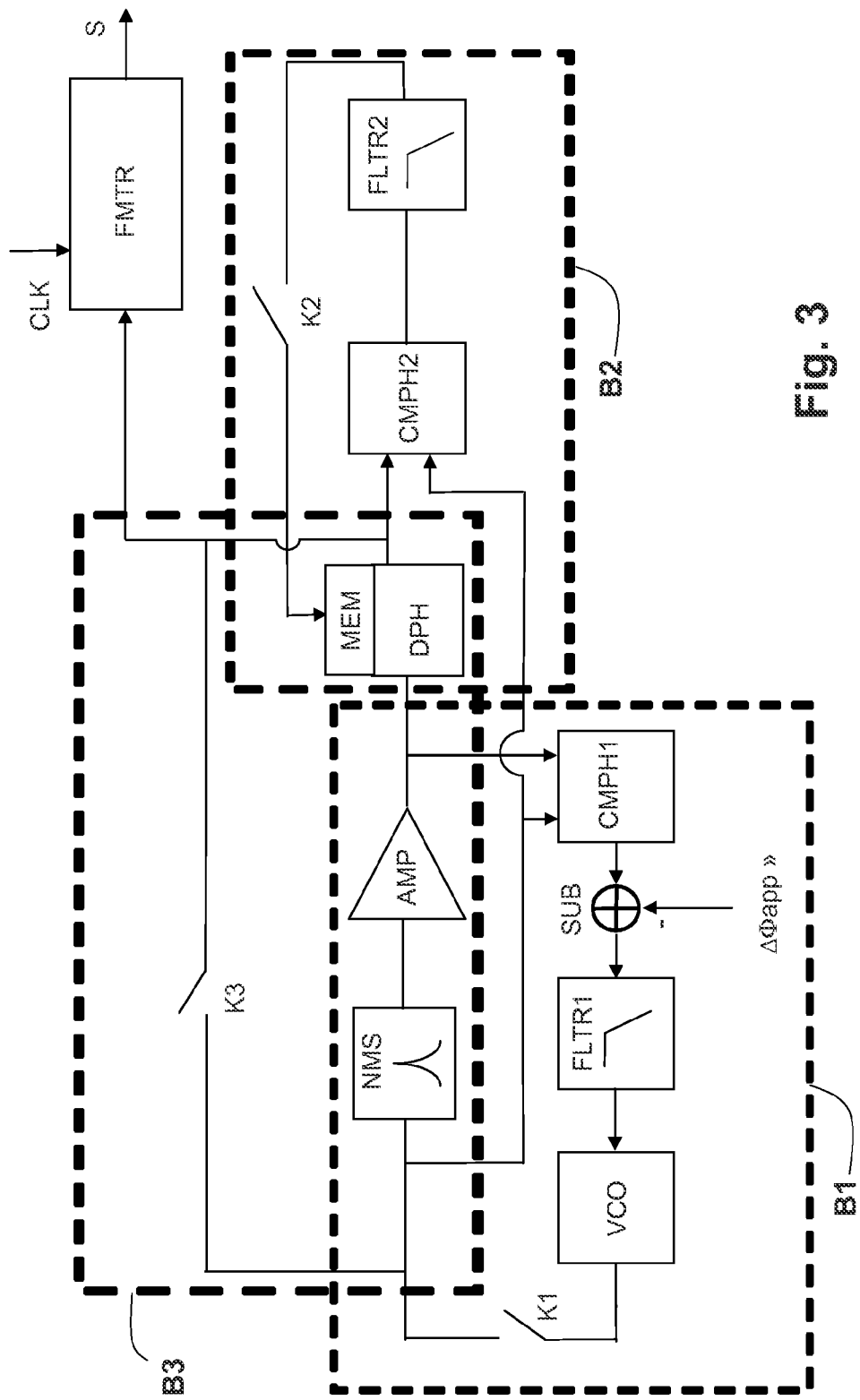
FIG. 3 represents an oscillating circuit according to the invention.

FIG. 3 represents a block diagram of the circuit according to the invention making it possible to measure the resonant frequency of a nanoresonator.

It consists of three feedback loops B1, B2, B3 each represented in a respective dashed-outline rectangle. Each of these loops can be enabled or disabled independently. The enabling or disabling of each loop is schematically represented here by a respective switch K1, K2, K3 which connects (enables the loop) or disconnects (disables the loop) a feedback link specific to each loop.

Figure 2:
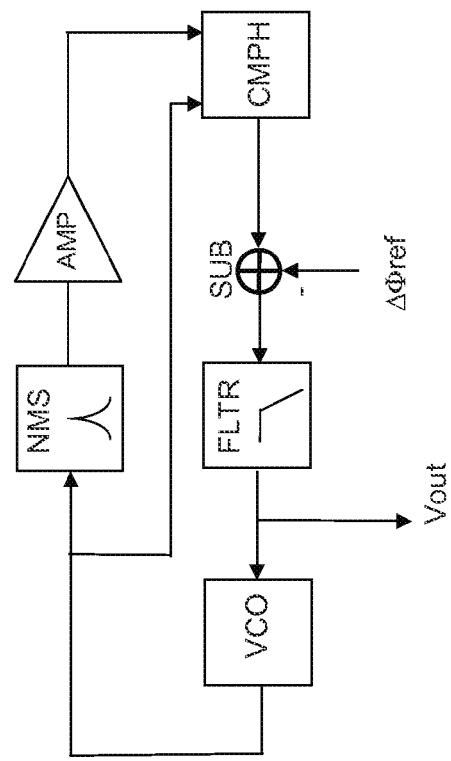
FIG. 2, already described, represents a nanoresonator oscillating circuit, comprising a phase-locked loop.

The first loop B1 is a phase-locked loop similar to that of FIG. 2. It comprises a nanoresonator NMS, an amplifier AMP, a controlled frequency oscillator VCO which can be controlled by an analogue voltage or by a digital command, a phase comparator CMPH1 and a subtractor SUB. To simplify the explanations, it is considered that the control of the oscillator VCO is analogue. The oscillator VCO serves as excitation source for the resonator, that is to say that its output is linked to an excitation input of the resonator. The amplifier AMP amplifies the output signal of the resonator. The phase comparator CMPH1 supplies an analogue or digital measurement of the phase difference between the signals present on its inputs, namely on a first input, the excitation signal of the resonator, and on a second input, the output signal of the amplifier. The analogue or digital output of the phase comparator is applied to a subtractor SUB which subtracts from the measurement made by the comparator a value $\Delta\Phi app$. This value is an estimated value of the phase shift introduced by the resonator and the amplifier at the resonant frequency. This value can be approximate. It makes it possible to check that the conditions are fairly close to the natural oscillation conditions of the resonator; it can be obtained by a prior characterization in open loop mode or by the knowledge of the general characteristics of the resonator, but it does not need to be exact and in particular it does not need to take account of the dispersion between the real characteristics of different resonators with the same nominal characteristics.

A low-pass filter FLTR1 can be provided to ensure the stability of the loop, between the output of the subtractor and a control input of the VCO oscillator.

The switch K1 which makes it possible to enable or disable the first loop B1 is placed between the output of the oscillator VCO and the excitation input of the resonator; it could be placed at other positions but with care taken, however, to ensure that the disabling of the loop B1 must not prevent the enabling of the third loop B3 which also uses the resonator NMS and the amplifier AMP.

When the loop B1 is in service, the oscillator automatically adjusts its frequency to the resonant frequency of the resonator NMS: if the frequency of the oscillator is too low, the phase comparator supplies a value which increases and which tends to raise the oscillation frequency.

The second feedback loop B2 comprises a controllable phase shifter DPH, a second phase comparator CMPH2, a stabilizing low-pass filter FLTR2, and a memory MEM that can store a phase shift value control setpoint.

The phase shifter DPH receives the output of the amplifier AMP and applies to the output signal of the amplifier a phase shift which is defined by the content of the memory MEM. When the loop B2 is enabled, the content of the memory can vary and is automatically locked in a direction which cancels the phase shift between the inputs of the phase comparator CMPH2. When it is disabled, the content of the memory MEM is fixed at the value taken when the loop was enabled. The output of the phase shifter is applied to a first input of the second phase comparator CMPH2. The excitation signal for the resonator NMS is applied to another input of the second phase comparator. The output of the second phase comparator is applied to the filter FLTR2 and from there to the memory MEM if the loop B2 is enabled. The switch K2 which defines the enabling or disabling of the loop B2 is represented by a switch inserted into the link between the output of the filter FLTR2 and the input of the memory MEM. When it is closed, the loop B2 is enabled. When it is open, it is disabled.

When the loop B2 is enabled, the second phase comparator CMPH2 supplies a measurement of the phase difference between the output of the phase shifter DPH and the excitation input of the resonator. It locks the control of the phase shifter in a direction tending to return to zero (modulo $2\pi$) this phase difference, that is to say that the memory MEM receives a control value (analogue or preferably digital) such that the phase shift introduced by the phase shifter precisely compensates the phase shift of the resonator and of the amplifier. When the feedback loop B2 is no longer enabled (that is to say it no longer provides feedback), the memory MEM imposes this compensation phase shift on the phase shifter DPH.

The third loop B3 comprises the series assembly of the resonator NMS, the amplifier AMP, and the controllable phase shifter DPH, and a direct feedback link between the output of the phase shifter DPH and the input of the resonator NMS. This link can be broken by the switch K3 if the loop B3 has to be disabled. When the loop B3 is enabled (the other two loops being disabled), the assembly of the resonator, the amplifier, the phase shifter and the feedback link switches to self-oscillation mode at the resonant frequency of the resonator. The phase shift introduced by the phase shifter DPH under the control of the setpoint stored in the memory precisely compensates the phase shift exhibited by the resonator and the amplifier at the resonant frequency. The natural oscillation conditions (phase shift that is a multiple of $2\pi$ and gain greater than or equal to 1 obtained by the amplifier) are met.

In a calibration phase, the third loop is broken by the switch K3 whereas the other two loops are enabled. The phase-locked loop B3 establishes an oscillation at the resonant frequency of the resonator and the loop B2 locks the value of the phase shift of the phase shifter DPH and stores the control needed to obtain a phase shift that is a multiple of $2\pi$ between the input of the resonator and the output of the phase shifter. In the operation phase, the two loops B1 and B2 are disabled by the switches K1 and K2 but the phase-shift control is retained in memory. The third loop B3 is enabled and maintains the self-oscillation by using the control placed in memory.

The oscillation frequency can then be measured by the frequency meter FTMR. The latter can operate by counting pulses of a clock CLK at a frequency very much greater than the resonant frequency.

Figure 4:
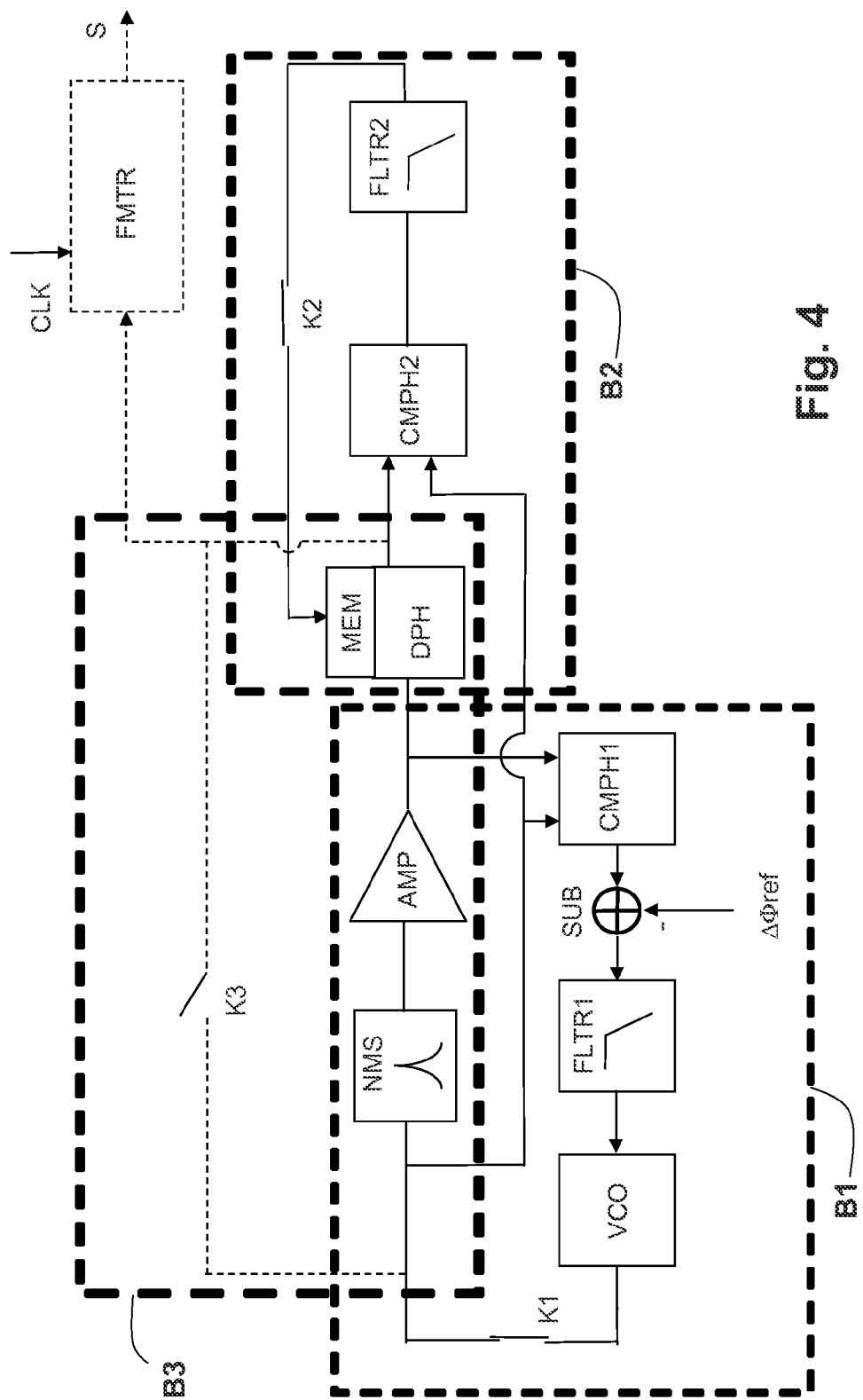
FIG. 4 represents the oscillating circuit configured for a calibration phase.
Figure 5:
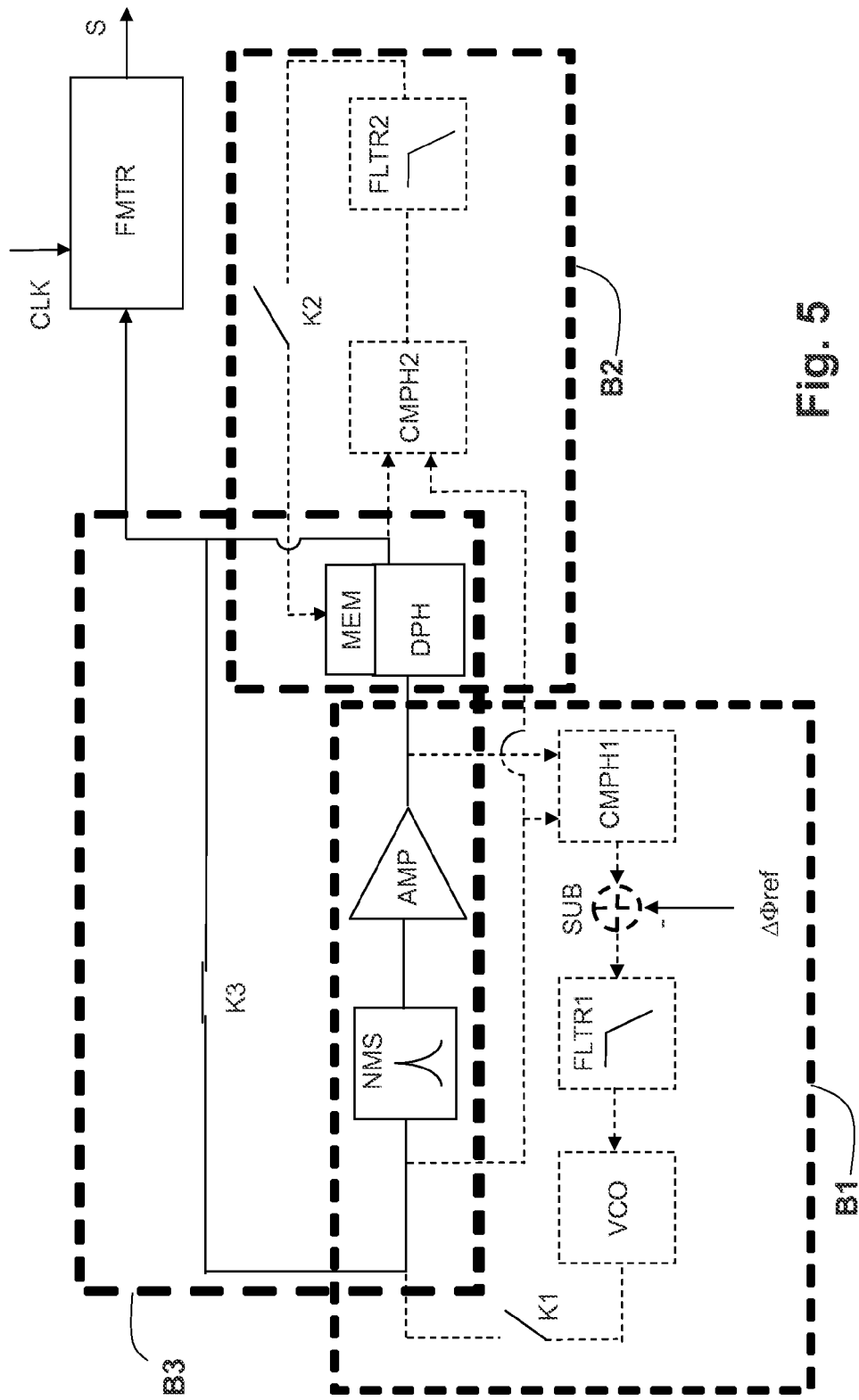
FIG. 5 represents the oscillating circuit configured for a resonant frequency measurement phase.

FIG. 4 represents the configuration of the circuit according to the invention in the calibration phase. FIG. 5 represents the configuration of the circuit in the operation phase. In these two figures, the circuit elements that are not used are represented by broken lines.

Figure 6:
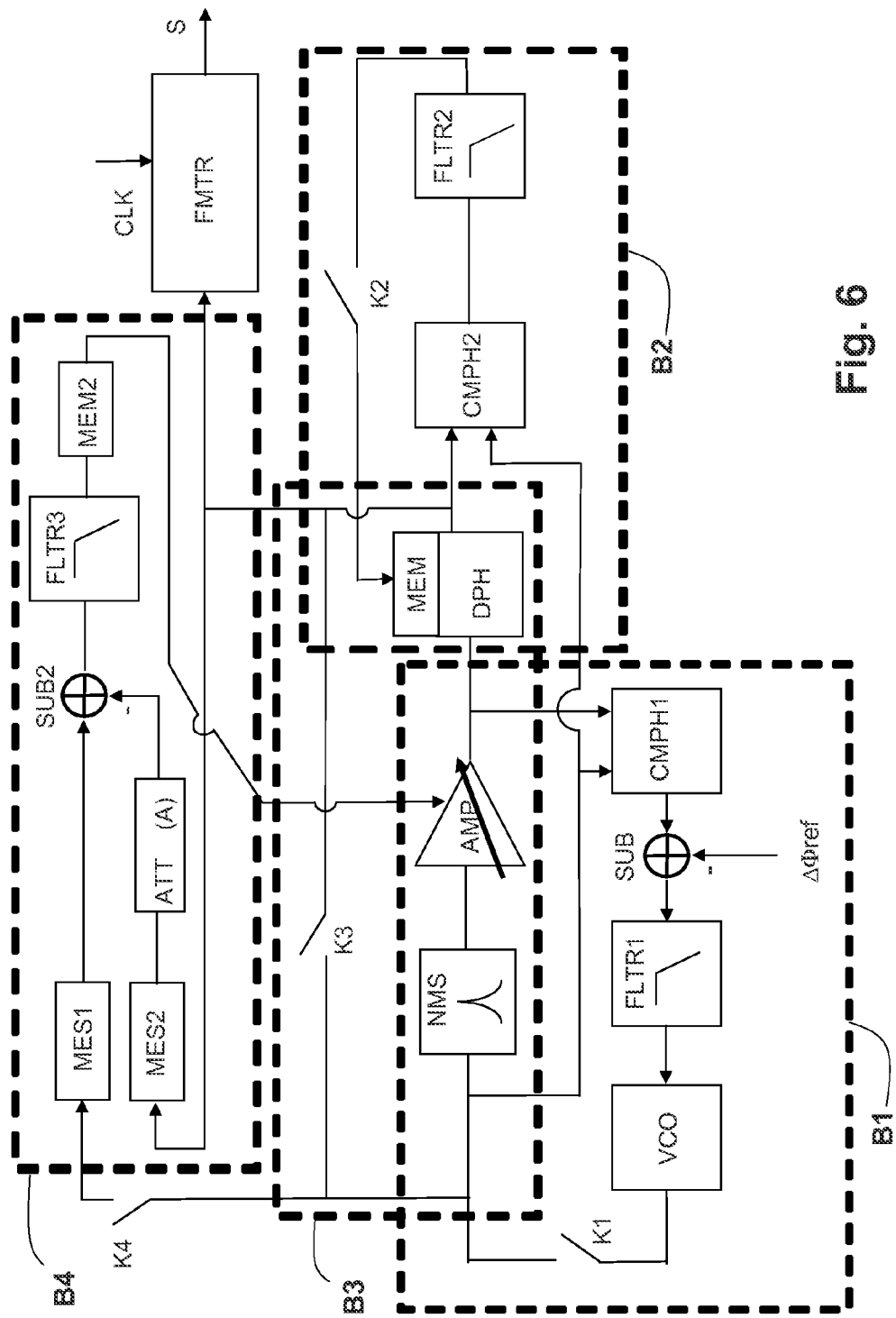
FIG. 6 represents a variant embodiment with gain control.

FIG. 6 represents a variant embodiment in which an additional feedback loop B4 has been added, the role of which is to establish an appropriate gain for the amplifier AMP in order to ensure the loop gain conditions necessary for the self-oscillation of the loop B3. These conditions are less critical than the phase conditions but it is advantageous to take them into account.

The amplifier AMP is, in this configuration, an amplifier with controlled variable gain. The feedback loop establishes an appropriate gain during the gain calibration phase, which occurs at the same time as the phase shift calibration phase. The control for obtaining this gain is stored in a memory MEM2. In an operation phase, the feedback loop B4 is disabled but the stored gain control value is retained and used to control the amplifier operating in the third loop B3 and impose on it the gain defined in the calibration phase.

In order to establish the appropriate gain, it is possible to measure (measurement circuits MES1 and MES2) the signal amplitudes, for example the peak amplitudes, using peak detectors, at the input of the resonator NMS and at the output of the phase shifter DPH, and it is possible to perform regulation by subtraction (subtractor SUB2) between the signal levels at the input of the resonator and at the output of the phase shifter DPH to return to a predefined gain value, equal to or greater than 1, the ratio between these two signal levels. During the calibration phase, the loop B4 is enabled and locks the gain on a setpoint value which can be equal to 1 or preferably greater than 1. A gain different from the setpoint value is reflected in a modification of the gain control of the amplifier in a direction tending to return the gain to the setpoint value. If the measurement circuits MES1 and MES2 supply the same measurement level for one and the same signal level applied to their input, the gain setpoint is defined from the attenuation A (A<1) of an attenuator ATT connected in series with the measurement circuit MES2 on the negative input of the subtractor SUB2: the locking of the loop B4 tends to impose a gain setpoint on the amplifier AMP such that the gain of the series assembly of the resonator, the amplifier, and the phase shifter tends towards a value equal to 1/A. The presence of the attenuation A ensures a gain margin for the loop B3 when it is enabled, to guarantee that its gain remains greater than or equal to 1 despite the technological dispersions.

Figure 1:
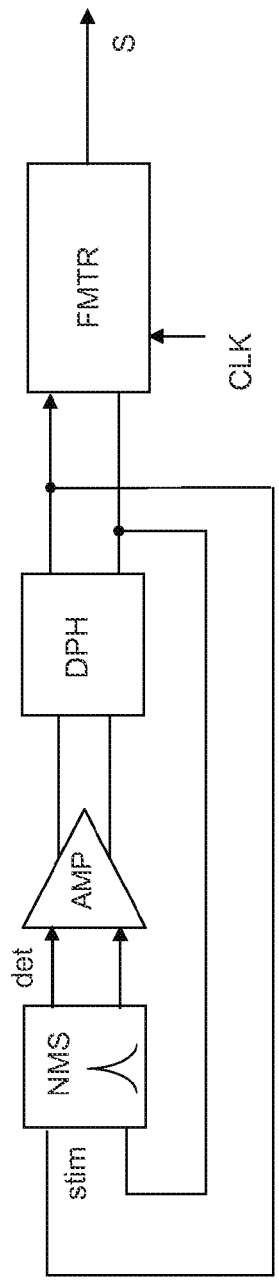
FIG. 1, already described, represents a self-oscillating circuit with nanoresonator.

It will be noted that the circuit according to the invention, although it employs a phase-locked loop, consuming more energy than a simple self-oscillating circuit such as that of FIG. 1, has a relatively limited consumption because the phase-locked loop operates only during the calibration phase.

The invention is of particular interest in the case of a network of resonators, for example a matrix network of rows and columns of resonators.

At each point $P_{i,j}$ of the network at the intersection of a row number i and of a column number j, an individual oscillating circuit is provided corresponding to the loop B3, that is to say a circuit $B3_{i,j}$ comprising a resonator $NMS_{i,j}$, an amplifier $AMP_{i,j}$, a phase shifter $DPH_{i,j}$, and an individual phase control memory $MEM_{i,j}$. These elements can be of small dimensions and low electrical consumption in the absence of phase-locked loop.

Figure 7:
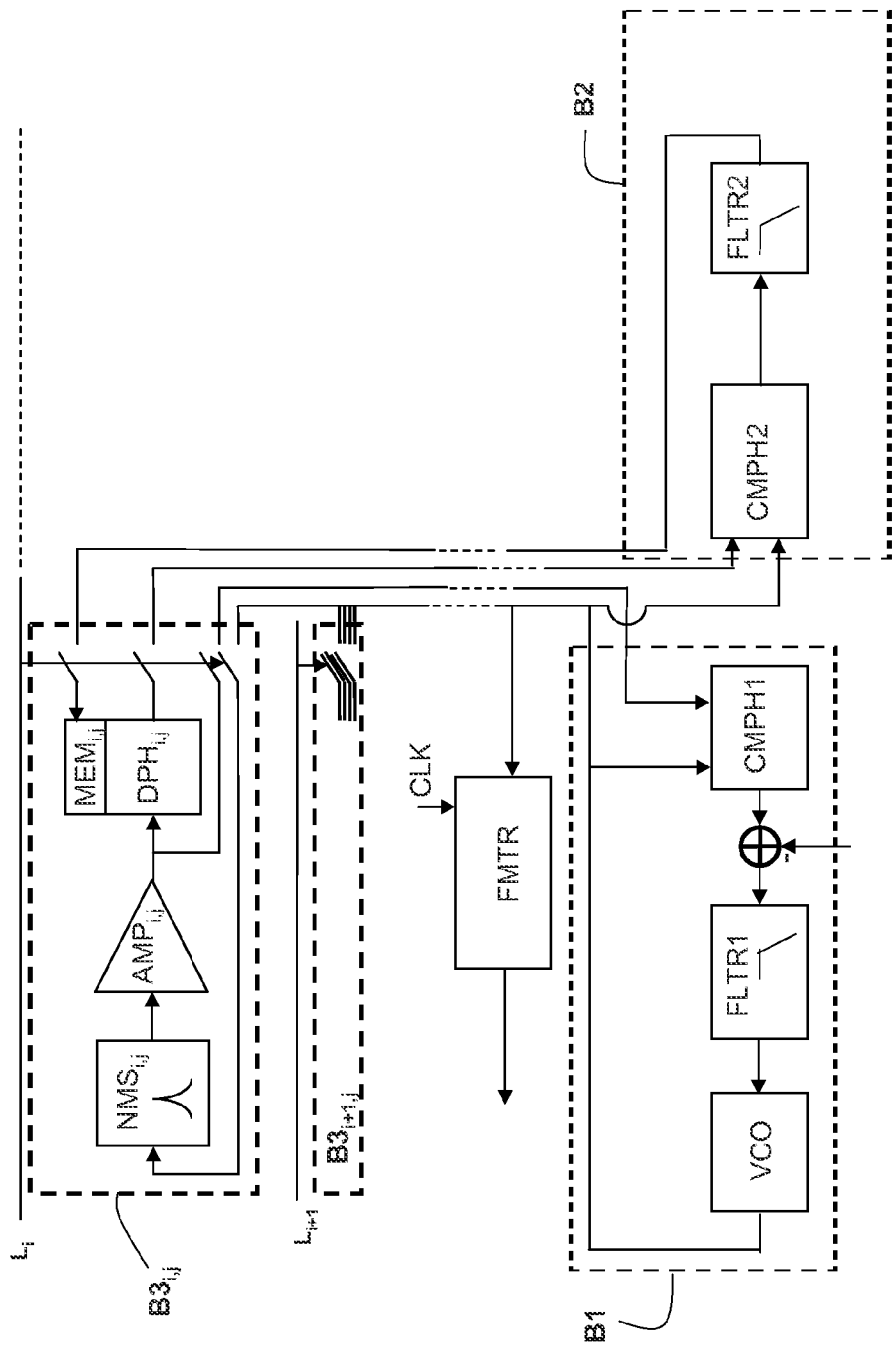
FIG. 7 represents a use of the invention in the context of a matrix network of nanoresonators using a first and a second feedback loop common to all the pixels and a third self-oscillation loop specific to each nanoresonator.

However, the loops B1 and B2 used in the calibration phases can be common to all the points of one and the same column of resonators, even to all the columns. FIG. 7 represents an organisational diagram of such a matrix of resonators. It is assumed, for simplicity, that there is no gain hunting loop B4, but such a loop could be envisaged.

Four column conductors associated with each respective column can be provided. The individual circuits of each point are addressable individually by row to refer the appropriate signals to each of the column conductors. The circuits at the foot of a column (loops B1, B2) use the signals present on the column conductors (or apply signals to the column conductors).

A first column conductor links, when the row number i is addressed, the input of the resonator $NMS_{i,j}$ to an input of the phase comparator CMPH1 of the loop B1 at the foot of a column, to an input of the phase comparator CMPH2 of the loop B2, to the output of the oscillator VCO of the loop B1, and to an input of a frequency meter FMTR.

A second column conductor links, when the row number i is addressed, the output of the amplifier $AMP_{i,j}$ to the second input of the phase comparator CMPH1 of the loop B1.

A third column conductor links, when the row number i is addressed, the output of the phase shifter $DPH_{i,j}$ to the second input of the phase comparator CMPH2 of the loop B2.

A fourth column conductor links, when the row number i is addressed, the phase control memory $MEM_{i,j}$ to the output of the loop B2 (that is to say the output of the filter FLTR2).

FIG. 7 does not show the switches for enabling or disabling the loops B1, B2 (external to the matrix of points) and B3 (located at each point).

The filters FLTR1 and FLTR2 can be relatively bulky digital filters (including analogue-digital converters) because they are external to the matrix of resonators.

The operation of the matrix can consist in a rotating addressing of the successive rows, the addressing of one and the same determined row successively including a calibration phase, with storage at each point of a respective phase-shift control, and an operation phase using the stored control and transmitting a signal at resonance frequency to the frequency meter.

However, it is also possible to envisage first of all performing a successive addressing of all the rows during a calibration phase with storage of the phase-shift controls, followed by a successive addressing of all these rows during an operation phase using the stored control.

It will be noted that, in the circuit according to the invention, the phase shifter can be analogue controlled or digitally controlled, the advantage of digital control being that the phase-shift control determined during the calibration phase can be stored more easily (with a very small circuit of a few SRAM memory points).

Figure 8:
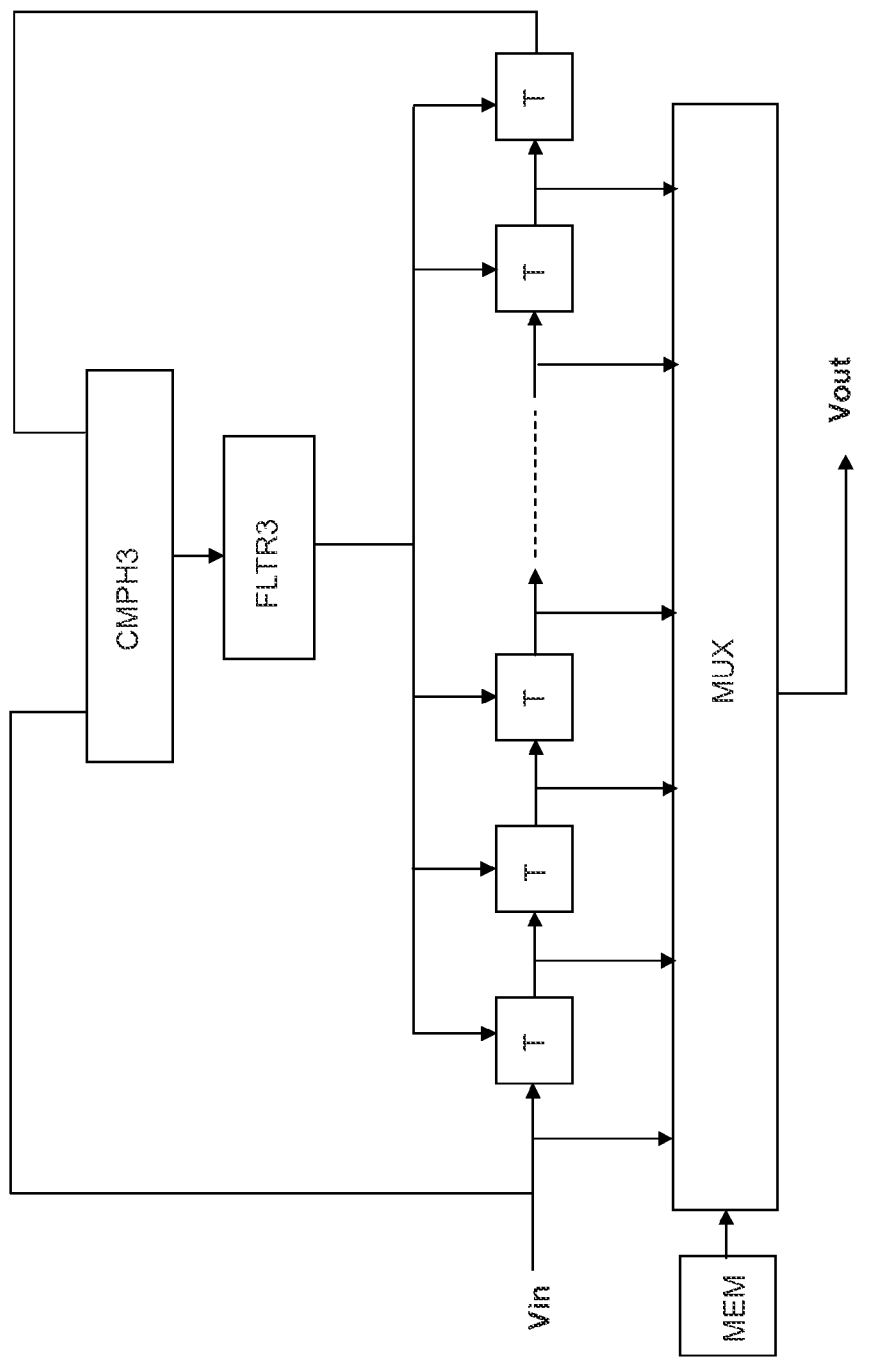
FIG. 8 represents a digitally-controlled phase shifter that can be used in the invention.

A digitally-controlled phase shifter can be produced, for example, in the manner represented in FIG. 8, with a delay-locked loop comprising a series of N elements with delay T, all identical, and all adjustable by one and the same control voltage. This control voltage is derived from a phase comparator and a filter. The first delay element receives an input signal Vin to be phase shifted. The phase comparator receives the input Vin of the first delay element and the output of the last. It establishes, by feedback, a control voltage Vctl which cancels the phase between its two inputs, which establishes a phase shift of $2\pi$ between the input and the output of the series of delay elements. The phase shift established by each delay element is $2\pi/N$. A multiplexer MUX controlled by the content of a memory selects the first phase shifter to establish an output signal Vout of phase shift $2\pi/N$ relative to the input signal.

The invention claimed is:

1. An electronic circuit for measuring an oscillation frequency of a resonator, comprising a first feedback loop which is a phase-locked loop comprising the resonator, a controlled oscillator and a first phase comparator, said first feedback loop locking an output frequency of the controlled oscillator at a resonant frequency of the resonator, said electronic circuit further comprising:
a second feedback loop comprising a controllable phase shifter, a second phase comparator receiving the output of the controlled oscillator and the output of the controllable phase shifter, and the second phase comparator supplying a control signal for the phase shifter acting in a direction tending to reduce to zero a phase shift between its inputs, means being provided for storing the obtained phase-shift control signal,
a self-oscillation loop comprising the resonator and the controllable phase shifter and linking the output of the controllable phase shifter to the input of the resonator,
and means for activating the first feedback loop and the second feedback loop and deactivating the self-oscillation loop, during a calibration phase, and for deactivating the first and the second feedback loops and activating the self-oscillation loop, during an operation phase, the control signal of the controllable phase shifter during the operation phase being the control signal stored at the end of the calibration phase.

2. The electronic measurement circuit according to claim 1, wherein the first feedback loop comprises the resonator in series with an amplifier, the first phase comparator receiving, on one input, the output of the amplifier and, on another input, the output of the controlled frequency oscillator and supplying a measurement of the phase shift between its inputs, a subtractor for subtracting from this measurement of the phase shift a reference phase-shift value, the output of the subtractor controlling the controlled-frequency oscillator.

3. The electronic measurement circuit according to claim 1, wherein a low-pass filter is provided in the first feedback loop between an output of the subtractor and a control input of the controlled oscillator.

4. The electronic measurement circuit according to claim 2, wherein a low-pass filter is provided in the first feedback loop between an output of the subtractor and a control input of the controlled oscillator.

5. The electronic measurement circuit according to claim 1, wherein a low-pass filter is provided in the second feedback loop between an output of the second phase comparator and the control storage means of the phase shifter.

6. The electronic measurement circuit according to claim 2, wherein a low-pass filter is provided in the second feedback loop between an output of the second phase comparator and the control storage means of the phase shifter.

7. The electronic measurement circuit according to claim 3, wherein a low-pass filter is provided in the second feedback loop between an output of the second phase comparator and the control storage means of the phase shifter.

8. The electronic measurement circuit according to claim 4, wherein a low-pass filter is provided in the second feedback loop between an output of the second phase comparator and the control storage means of the phase shifter.

9. The electronic measurement circuit according to claim 1, further comprising a third feedback loop enabled during the calibration phase, for establishing a gain control signal for the amplifier such that the gain of the subsystem comprising the resonator, the amplifier and the phase shifter is greater than 1 during the calibration phase, and a means for storing this gain control signal and for applying the stored control signal to the amplifier during the operation phase.

10. The electronic measurement circuit according to claim 2, further comprising a third feedback loop enabled during the calibration phase, for establishing a gain control signal for the amplifier such that the gain of the subsystem comprising the resonator, the amplifier and the phase shifter is greater than 1 during the calibration phase, and a means for storing this gain control signal and for applying the stored control signal to the amplifier during the operation phase.

11. The electronic measurement circuit according to claim 3, further comprising a third feedback loop enabled during the calibration phase, for establishing a gain control signal for the amplifier such that the gain of the subsystem comprising the resonator, the amplifier and the phase shifter is greater than 1 during the calibration phase, and a means for storing this gain control signal and for applying the stored control signal to the amplifier during the operation phase.

12. The electronic measurement circuit according to claim 1, further comprising a network of rows and columns of resonators, the third self-oscillation loop being individual for each resonator and being addressable by a row conductor common to the resonators of one and the same row, the first and the second feedback loops being common to the resonators of one and the same column and being linked, by column conductors common to the resonators of one and the same column, to the elements of that of the third loops which is addressed by a row conductor.

13. The electronic measurement circuit according to claim 2, further comprising a third feedback loop enabled during the calibration phase, for establishing a gain control signal for the amplifier such that the gain of the subsystem comprising the resonator, the amplifier and the phase shifter is greater than 1 during the calibration phase, and a means for storing this gain control signal and for applying the stored control signal to the amplifier during the operation phase.

14. The electronic measurement circuit according to claim 3, further comprising a third feedback loop enabled during the calibration phase, for establishing a gain control signal for the amplifier such that the gain of the subsystem comprising the resonator, the amplifier and the phase shifter is greater than 1 during the calibration phase, and a means for storing this gain control signal and for applying the stored control signal to the amplifier during the operation phase.

* * * * *